United States Patent [19]

Felder et al.

[11] 4,088,554
[45] May 9, 1978

[54] INITIATORS FOR PHOTOPOLYMERIZATION

[75] Inventors: Louis Felder, Basel; Rudolf Kirchmayr, Aesch; Daniel Bellus, Riehen, all of Switzerland

[73] Assignee: Ciba-Geigy Corporation, Ardsley, N.Y.

[21] Appl. No.: 751,305

[22] Filed: Dec. 16, 1976

[30] Foreign Application Priority Data

Dec. 23, 1975 Switzerland .................... 16701/75

[51] Int. Cl.² ............................ C08F 8/00; C08F 2/46
[52] U.S. Cl. ............................ 204/159.15; 96/115 P;
204/159.14; 204/159.18; 204/159.23;
204/159.24; 260/559 R; 260/561 B; 427/54;
560/115; 560/121; 560/126
[58] Field of Search .................. 204/159.15, 159.19,
204/159.23, 159.24; 96/115; 560/53

[56] References Cited

U.S. PATENT DOCUMENTS

| | | |
|---|---|---|
| 3,657,088 | 4/1972 | Heine et al. .................... 204/159.23 |
| 3,715,293 | 2/1973 | Sandner et al. ................. 204/159.14 |
| 3,801,329 | 4/1974 | Sandner et al. ................. 96/115 P |
| 3,937,722 | 2/1976 | Heine et al. .................... 260/465 F |
| 3,998,712 | 12/1976 | Hickmann et al. ............. 204/159.15 |
| 4,007,209 | 2/1977 | Hickmann et al. ............. 260/345.9 |
| 4,038,164 | 7/1977 | Via ................................ 204/159.15 |

Primary Examiner—Richard B. Turer
Attorney, Agent, or Firm—Vincent J. Cavalieri

[57] ABSTRACT

Monoketals of esters and amides of aromatic $\alpha,\beta$-dioxocarboxylic acids having the formula

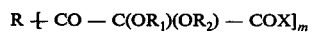

$$R + CO - C(OR_1)(OR_2) - COX]_m$$

wherein $m$ is 1 or 2, R is a mono- or divalent aromatic residue, $R_1$ and $R_2$ are monovalent organic residues and X is an alkoxy or amino groups, are photoinitiators for the UV-curing of resins. Examples for such resins are acrylates, methacrylates or unsaturated polyesters. The most important application for such photochemical curing is the field of coatings and printing inks.

15 Claims, No Drawings

INITIATORS FOR PHOTOPOLYMERIZATION

The invention relates to the use of α-monoketals of α,β-dioxocarboxylic acid derivatives as initiators for the photopolymerisation of unsaturated compounds and to photopolymerisable systems which contain such monoketals and contain unsaturated compounds. Specifically, the said carboxylic acid derivatives are esters and amides of these acids.

Photochemical polymerisation processes have achieved considerable importance industrially, above all in those cases where thin layers have to be cured within a short time, such as, for example, in the curing of lacquer coatings or when drying printing pastes. Compared with conventional curing processes, UV irradiation in the presence of photo-initiators displays a number of advantages, the most important of which is certainly the high rate of photo-curing. The rate is highly dependent on the photo-initiator used and there has been no lack of attempts to replace the conventional initiators by ever better and more effective compounds. The most effective photo-initiators include derivatives of benzoin, above all benzoin ethers, such as are described, for example, in British Patent Specification Nos. 1,213,498, 1,254,231 and 1,156,460 or in Swiss Patent No. 511,902. Ketals of benzil have been proposed as photo-initiators in U.S. Pat. No. 3,715,293 and in German Offenlegungsschriften No. 2,232,365 and 2,337,813 and, finally, semi-ketals of 1,2,3-triketones have also already been mentioned in German Offenlegungsschrift No. 2,457,575.

Disadvantages to which the known photo-initiators are subject are, in part, the inadequate stability to storage in the dark of the photopolymerisable systems mixed with such initiators. Some benzoin derivatives tend to yellow the cured compositions and the same also applies to some derivatives of diketones and triketones. Other initiators possess an inadequate reactivity, which manifests itself in relatively long curing times, or they are too sparingly soluble in the photopolymerisable systems or they are rapidly deactivated by atmospheric oxygen. There is therefore a need in industry for photo-initiators which are readily soluble in the substrate and, whilst having a good stability to storage in the dark, initiate photopolymerisation more rapidly and give a higher polymer yield per unit time than the known photo-initiators. The use of improved photo-initiators of this type would enable the costly industrial UV irradiation equipment to be better utilised.

It has been found that compounds of formula I which follows possess the required properties as photo-initiators and do not display the disadvantages described, or display these disadvantages to a substantially lesser extent than the known photo-initiators. The invention relates to the use of monoacetals of α,β-dioxocarboxylic acid derivatives of the formula I

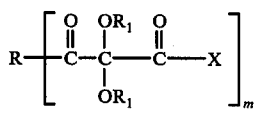

in which $m$ is 1 or 2, R, when $m$ is 1, denotes a phenyl radical which can be substituted by one or more of the groups: alkyl with 1-4 C atoms, alkoxy or alkylthio with 1-4 C atoms, alkoxyalkyl with 2-4 C atoms, acylamino with 1-4 C atoms or halogen, or denotes a pyridyl radical and, when $m$ is 2, represents phenylene, $R_1$ represents alkyl with 1-6 C atoms, alkoxyalkyl with 3-6 C atoms, cycloalkyl with 5-7 C atoms, phenylalkyl with 7-9 C atoms, furfuryl, tetrahydrofurfuryl or phenyl, which can be substituted by one or more of the groups: alkyl with 1-4 C atoms, alkoxy or alkylthio with 1-4 C atoms, alkoxyalkyl with 2-4 C atoms, halogen or acylamino with 1-4 C atoms, X represents a group —OR$_2$ or —N(R$_3$)(R$_4$), in which R$_2$ either represents one of the substituents mentioned for R$_1$ or is alkyl with 7-18 C atoms and R$_3$ and R$_4$ independently of one another represent hydrogen, alkyl with 1-4 C atoms, alkoxyalkyl with 3-6 C atoms or hydroxyalkyl with 2-4 C atoms.

In these formulae R and R$_1$ can denote a substituted phenyl radical. Examples of such radicals are the tolyl, xylyl, 4-isopropylphenyl, t-butylphenyl, anisyl, ethoxyphenyl, 2,4-dimethoxyphenyl, 4-butylthiophenyl, methoxymethyl-phenyl, 3-acetylaminophenyl, chlorophenyl, 3,4-dibromophenyl or fluorophenyl radicals.

R$_1$ can be a lower alkyl radical, such as, for example, methyl, ethyl, propyl, butyl or hexyl; R$_1$ can also be alkoxy-alkyl, such as, for example, methoxyethyl, methoxypropyl or butoxyethyl.

When R$_1$ denotes cycloalkyl it can be, for example, cyclopentyl, cyclohexyl or methylcyclohexyl.

When R$_1$ denotes phenylalkyl it can be, for example, benzyl, methylbenzyl, phenylethyl or phenylpropyl.

If the compounds of the formula I are esters, X is a group —OR$_2$ in which R$_2$ can denote an alkyl radical with 1-18 C atoms, for example methyl, ethyl, isopropyl, butyl, isooctyl, 2-ethylhexyl, n-dodecyl or octadecyl.

If the compounds of the formula I are amides, X is a group —N(R$_3$)(R$_4$) and, within the scope of the given definition for R$_3$ and R$_4$, this can be a NH$_2$ group or a primary or secondary amino group. For example, X can be the methylamino, dimethylamino, methyl-butylamino, di-isopropyl-amino, tert.-butylamino, di-(hydroxyethyl)-amino, methyl-hydroxyethyl-amino, di-(methoxyethyl)-amino, propyl-methoxyethyl-amino or di-(2-hydroxypropyl)-amino group.

Amongst the compounds which can be used according to the invention, compounds of the formula I in which $m$ is 1 or 2, R denotes a phenyl radical which can be substituted by CH$_3$, OCH$_3$, SCH$_3$ or Cl, or R represents a phenylene radical, X is a group —OR$_2$ and R$_1$ and R$_2$ are identical and each denote an alkyl group with 1-4 C atoms are preferred.

Examples of esters of the formula I are: ethyl α-diethoxy-benzoylacetate, ethyl α-diethoxy-4-chlorobenzoylacetate, ethyl α-diethoxy-2-methoxybenzoylacetate, ethyl α-diethoxy-4-ethoxybenzoylacetate, ethyl α-diethoxy-3-acetylaminobenzoylacetate, methyl α-dimethoxy-4-methoxymethylbenzoylacetate, methyl α-dimethoxy-2,4-dichlorobenzoylacetate, methyl α-dimethoxy-4-tert.-butylbenzoylacetate, methyl α-dimethoxy-p-tolyloylacetate, methyl α-dimethoxy-nicotinoylacetate, benzene-1,4-bis-(ethyl β-oxo-α-diethoxypropionate), butyl α-dibutoxy-benzoylacetate, cyclohexyl α-dicyclohexyloxy-benzoylacetate, benzyl α-dibenzyloxy-benzoylacetate, tetrahydrofurfuryl α-di-(tetrahydrofurfuryloxy)-benzoylacetate, phenyl α-diphenoxy-benzoylacetate, benzyl α-di-(4-tolyloxy)-benzoylacetate, dodecyl α-dimethoxy-4-methoxybenzoylacetate and octadecyl α-diethoxy-benzoylacetate.

Examples of amides of the formula I are: α-dimethoxybenzoylacetamide, N-butyl-α-dimethoxy-benzoylacetamide, N-dimethyl-α-dimethoxy-benzoylacetamide, N-di-hydroxyethyl-α-dimethoxy-benzoylacetamide, N-di-methoxypropyl-α-dimethoxybenzoylacetamide and N-methyl-α-dimethoxy-benzoylacetamide.

Amongst the compounds of the formula I, only the compound in which R is phenyl, $R_1$ is methyl and X is —$OCH_3$ is known, specifically from German Offenlegungsschrift 1,286,037 and from Chem. Berichte 99, 1899–1905 (1966). The present invention therefore also comprises the compounds of the formula I

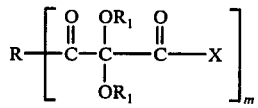

in which $m$ is 1 or 2, R, when $m$ is 1, denotes a phenyl radical, which can be substituted by one or more of the groups: alkyl with 1–4 C atoms, alkoxy or alkylthio with 1–4 C atoms, alkoxyalkyl with 2–4 C atoms, acylamino with 1–4 C atoms or halogen, or denotes a pyridyl radical and, when $m$ is 2, represents phenylene, $R_1$ represents alkyl with 2–6 C atoms, alkoxyalkyl with 3–6 C atoms, cycloalkyl with 5–7 C atoms, phenylalkyl with 7–9 C atoms, furfuryl, tetrahydrofurfuryl or phenyl, which can be substituted by one or more of the groups: alkyl with 1–4 C atoms, alkoxy or alkylthio with 1–4 C atoms, alkoxyalkyl with 2–4 C atoms, halogen or acylamino with 1–4 C atoms, X is a group —$OR_2$ and $R_2$ is the same as $R_1$, and also compounds of the formula I in which $m$ and R have the above-mentioned meaning, $R_1$ represents alkyl with 1–6 C atoms, alkoxyalkyl with 3–6 C atoms, cycloalkyl with 5–7 C atoms, phenylalkyl with 7–9 C atoms, furfuryl, tetrahydrofurfuryl or phenyl, which can be substituted by one or more of the groups: alkyl with 1–4 C atoms, alkoxy or alkylthio with 1–4 C atoms, alkoxyalkyl with 2–4 C atoms, halogen or acylamino with 1–4 C atoms, X represents a group —$OR_2$ or —$N(R_3)(R_4)$, in which $R_2$ differs from $R_1$ and is either one of the substituents mentioned for $R_1$ or alkyl with 7–18 C atoms, and $R_3$ and $R_4$ independently of one another represent hydrogen, alkyl with 1–4 C atoms, alkoxyalkyl with 3–6 C atoms or hydroxyalkyl with 2–4 C atoms, as well as compounds of the formula I in which $m$ is 1 or 2, R, when $m$ is 1, denotes a phenyl radical which is substituted by one or more of the groups: alkyl with 1–4 C atoms, alkoxy or alkylthio with 1–4 C atoms, alkoxyalkyl with 2–4 C atoms, acylamino with 1–4 C atoms or halogen, or denotes a pyridyl radical and, when $m$ is 2, represents phenylene, X represents a group —$OR_2$ and $R_1$ and $R_2$ are methyl.

A sub-group of these compounds comprises those compounds of the formula I in which X is a —$OR_2$ group and $R_2$ is identical to $R_1$. These esters (Ia) can be manufactured by the process described in German Offenlegungsschrift 1,286,037 by reacting an aromatic or heterocyclic carboxylic acid chloride (III) with a tetraorgano-oxy-ethylene (IV):

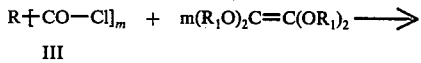

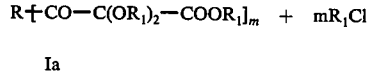

Another sub-group of the compounds of the formula I comprises those in which X is a —$OR_2$ group and $R_2$ differs from $R_1$. These esters Ib can be manufactured from the esters Ia by trans-esterification with the monohydroxy compounds $R_2OH$:

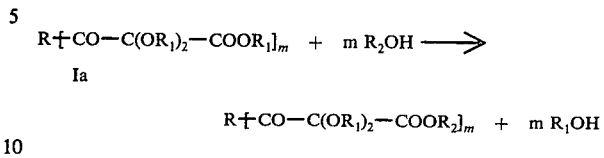

These trans-esterifications are advantageously carried out in the presence of customary trans-esterification catalysts, preferably basic catalysts, such as alkali metals, alkali metal alcoholates, alkali metal amides, alkali metal hydrides or alkali metal hydroxides or alkaline earth metals, alkaline earth metal alcoholates, alkaline earth metal amides, alkaline earth metal hydrides or alkaline earth metal hydroxides. Since trans-esterifications are equilibrium reactions, these proceed particularly readily when the hydroxy compound $R_2OH$ has a considerably higher boiling point than the hydroxy compound $R_1OH$ and the latter can thus be removed from the equilibrium by distilling off continuously.

A further sub-group of the compounds of the formula I comprises those in which X is a —$N(R_3)(R_4)$ group. These amides (Ic) can be manufactured from the esters of the formula Ia by reaction with compounds of the formula $(R_3)(R_4)NH$. In accordance with the definition of $R_3$ and $R_4$, these compounds can be ammonia or primary or secondary amines:

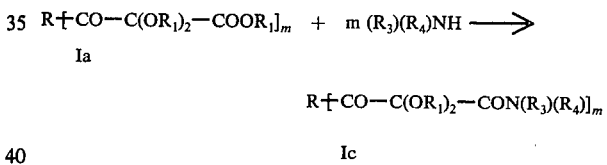

According to the invention, the compounds of the formula I and II can be used for the photopolymerisation of polymerisable unsaturated compounds or of systems which contain such compounds.

Such compounds are, for example, unsaturated monomers, such as esters of acrylic acid or methacrylic acid, for example methyl acrylate, ethyl acrylate, n- or tert.-butyl acrylate, isooctyl acrylate or hydroxyethyl acrylate, methyl methacrylate or ethyl methacrylate, ethylene diacrylate, neopentyl diacrylate, trimethylolpropane trisacrylate, pentaerythritol tetraacrylate or pentaerythritol trisacrylate; acrylonitrile, methacrylonitrile, acrylamide, methacrylamide and N-substituted (meth) acrylamides; vinyl esters, such as, for example, vinyl acetate, vinyl propionate, vinyl acrylate or vinyl succinate; other vinyl compounds, such as vinyl ethers, styrene, alkylstyrenes, halogenostyrenes, divinylbenzene, vinylnaphthalene, N-vinylpyrrolidone, vinyl chloride or vinylidene chloride; allyl compounds, such as diallyl phthalate, diallyl maleate, triallyl isocyanurate, triallyl phosphate or ethylene glycol diallyl ether and the mixtures of such unsaturated monomers.

Further photopolymerisable compounds are unsaturated oligomers or polymers and their mixtures with unsaturated monomers. These include thermoplastic resins which contain unsaturated groups, such as fumaric acid ester groups, allyl groups or acrylate or methacrylate groups. Usually, these unsaturated groups are bonded to the main chain of these linear polymers via functional groups. Mixtures of oligomers with monounsaturated and polyunsaturated monomers are of great importance. Examples of such oligomers are unsaturated polyesters, unsaturated acrylic resins and isocyanate-modified or epoxide-modified acrylate oligomers. Examples of polyunsaturated compounds are, above all, the acrylates of diols and polyols, for example hexamethylene diacrylate or pentaerythritol tetraacrylate. Acrylates, such as, for example, butyl acrylate, phenyl acrylate, benzyl acrylate, 2-ethyl-hexyl acrylate or 2-hydroxy-propyl acrylate, are also preferred as monounsaturated monomers. Choosing amongst the different representatives of the three components provides a means for varying the consistency of the unpolymerised mixture and the plasticity of the polymerised resin.

In addition to these three-component mixtures, two-component mixtures, above all, are very important in polyester resins. These two-component mixtures usually consist of an unsaturated polyester and a vinyl compound. The unsaturated polyesters are oligomeric esterification products of at least one unsaturated dicarboxylic acid, such as, for example, maleic acid, fumaric acid or citraconic acid, and usually at least one saturated dicarboxylic acid, such as, for example, phthalic acid, succinic acid, sebacic acid or isophthalic acid, with glycols, such as, for example, ethylene glycol, propane-1,2-diol, di- or tri-ethylene glycol or tetramethylene glycol, and in most cases monocarboxylic acids and monoalcohols are also additionally used for modification. These unsaturated polyesters are usually dissolved in a vinyl compound or allyl compound; styrene is preferably used for this purpose.

Photopolymerisable systems, such as are used for various purposes, usually contain a number of other additives in addition to the photopolymerisable compounds and the photo-initiator. Thus, it is frequently customary to add thermal inhibitors which, above all, are intended to protect the components against premature polymerisation during the production of the systems by mixing. Hydroquinone, p-methoxyphenyl, β-naphthylamine or β-naphthols, for example, are used for this purpose. Furthermore, small amounts of UV-absorbers, such as, for example, those of the benztriazole or benzophenone type, can be added.

In order to increase the stability to storage in the dark, copper compounds, such as copper naphthenate, copper stearate or copper octoate, phosphorus compounds, such as triphenyl phosphine, tributyl phosphine, triethyl phosphite, triphenyl phosphite or tribenzyl phosphate, quaternary ammonium compounds, such as tetramethylammonium chloride or trimethyl-benzylammonium chloride, or hydroxylamine derivatives, such as, for example, N-diethylhydroxylamine, can be added. Furthermore, the photopolymerisable systems can contain chain transfer agents, such as, for example, N-methyl-diethanolamine, triethanolamine or cyclohexene.

In order to exclude the inhibiting action of atmospheric oxygen, paraffin or similar wax-like substances are frequently added to photo-curable systems. Because of their lack of solubility in the polymer, these substances float up at the start of polymerization and form a transparent surface layer which prevents the admission of air. Inhibition due to atmospheric oxygen can also be reduced by introducing autoxidisable groups, for example allyl groups, into the resin to be cured.

Photopolymerisable systems also contain — depending on their intended use — fillers, such as silica, talc or gypsum, pigments, dyestuffs, fibres, agents which impart thixotropic properties, or levelling agents. Such additives, which are known and customary, are compatible with the photo-initiators according to the invention and do not impair their action.

Photo-curing is of great importance for printing pastes, since the drying time of the binder is a decisive factor for the rate of production of graphic products and should be of the order of fractions of a second. The initiators according to the invention are also very suitable for photo-curable systems for the manufacture of printing plates. In this case, mixtures of soluble linear polyamides with photopolymerisable monomers, for example acrylamides, and a photo-initiator are mostly used. Films or plates of these systems are exposed over the negative (or positive) of the print original and the uncured parts are then eluted with a solvent.

A further field of application of UV-curing is metal coating, for example when lacquer-coating sheet metal for tubes, tins or bottle closures.

Examples of UV-curing of paper coatings are the colourless lacquer-coating of labels, record sleeves or book jackets.

For the indicated fields of application, the compounds of the formula I and II are appropriately employed in amounts of 0.1 to 20% by weight and preferably of about 0.5 to 5% by weight, relative to the photopolymerisable system. System, in this context, signifies the mixture of the photopolymerisable compound, the photo-initiator and the other fillers and additives, which is used in the particular application.

The addition of the photo-initiators to the photopolymerisable systems is generally effected by simply stirring in since most of these systems are liquid or readily soluble. Usually, a solution of the initiators according to the invention results, by which means uniform distribution thereof and transparency of the polymers are ensured.

The polymerisation is carried out according to the known methods of photopolymerisation, by radiation with light which is rich in short-wave radiation. Suitable light sources are, for example, medium-pressure, high-pressure and low-pressure mercury vapour lamps and also super-actinic fluorescent tubes which have emission maxima in the range between 300 and 400 $\mu$.

The manufacture and use of the compounds of formula I is described in more detail in the examples which follow. In these examples, parts denote parts by weight, percentages denote percentages by weight and the temperature is given in degrees centigrade.

EXAMPLE 1

10.4 g (0.051 mol) of tetraethoxyethylene and 5.7 g (0.041 mol) of benzoyl chloride are warmed to 130° C under nitrogen for 16 hours. Distillation under a high vacuum gave 3 g of ethyl α-diethoxy-benzoyl-acetate as a yellowish oil.

Analysis $C_{15}H_{20}O_5$ Calculated C 64.27 H 7.19 O 28.54% Found C 63.9 H 7.2 O 28.5%.

The absorption maximum in UV is at 250 nm ($\epsilon$ = 15,900).

In the NMR spectrum, the following bands arise ($\delta$ in ppm): 2 aromatic H 8.2 (m), 3 aromatic H 7.5 (m), 4- methylene-H 3.62 (q), 6-methyl-H 1.21 (t), 2-methylene-H 4.08 (q) and 3-methyl-H 1.01 (t).

EXAMPLE 2

2.03 g (0.01 mol) of terephthalic acid chloride and 4.8 g (0.0236 mol) of tetraethoxyethylene were kept at 130° under nitrogen for 16 hours. All of the volatile constituents were removed at 100° under a water pump vacuum. The residue crystallised on the addition of hexane.

The resulting benzene-1,4-bis-(ethyl β-oxo-α-diethoxypropionate) was recrystallised once from isopropanol and once from ethanol. The purified compound were prepared analogously to Example 1 by reacting tetraethoxyethylene with different aromatic or heteroaromatic carboxylic acid chlorides. Their properties are given in Table 1.

Depending on their properties, the products were isolated by (a) distillation of the product under a high vacuum, (b) distilling off the constituents which are volatile in vacuo up to 150° and isolating the product as the residue, (c) as (b) with subsequent recrystallisation of the residue or (d) as (b) with subsequent purification of the residue by chromatography in a silica gel column.

Table 1

| Example | R | m | Isolation according to | Melting point | C calculated | C found | H calculated | H found | O calculated | O found |
|---|---|---|---|---|---|---|---|---|---|---|
| 3 | phenyl-OCH₃ | 1 | b | — | 61.9 | 62.4 | 7.15 | 7.2 | 30.9 | 30.7 |
| 4 | Cl-phenyl | 1 | a | — | 57.2 | 57.2 | 6.1 | 6.2 | 11.3 (Cl) | 11.8 |
| 5 | dimethylphenyl | 2 | d + a | — | 59.74 | 59.9 | 7.1 | 7.3 | 33.16 | 33.1 |
| 6 | pyridyl | 1 | d | 42–45° | 59.77 | 60.0 | 6.80 | 6.8 | 4.98 (N) | 5.1 | melts at 190–110°.

Analysis $C_{24}H_{34}O_{10}$ Calculated C 59.74 H 7.10%
Found C 60.0 H 6.9%

UV spectrum: $\alpha_{max}$ 264 nm, $\epsilon = 30,000$ NMR spectrum: 4H 8.2 (s), 8H 3.67 (q), 12H 1.34 (t), 4H 4.2 (q) and 6H 1.14 (t).

EXAMPLES 3–6

A number of compounds of the formula

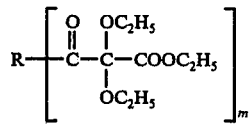

EXAMPLES 7–14

A number of compounds of the formula

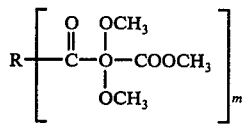

were prepared, analogously to Example 1, by reacting tetramethoxyethylene with carboxylic acid chlorides of the formula $R(COCl)_m$. Their properties are given in Table 2. The products were isolated by the methods a – d indicated for Examples 3–6.

Table 2

| Example | R | m | Isolation according to | Melting point | C calculated | C found | H calculated | H found | O calculated | O found |
|---|---|---|---|---|---|---|---|---|---|---|
| 7 | phenyl | 1 | a | — | — | — | — | — | — | — |
| 8 | H₃C-phenyl | 1 | a | — | — | — | — | — | — | — |

Table 2-continued

| Example | R | m | Isolation according to | Melting point | C calculated | C found | H calculated | H found | O calculated | O found |
|---|---|---|---|---|---|---|---|---|---|---|
| 9 | 4-methylphenyl (p-tolyl) | 2 | c (from ethanol) | 122–125° | 54.27 | 53.9 | 5.57 | 5.6 | — | — |
| 10 | phenyl | 1 | d + a | — | 54.27 | 54.4 | 5.57 | 5.4 | 40.16 | 40.2 |
| 11 | 4-chlorophenyl | 1 | a | — | — | — | — | — | — | — |
| 12 | 4-tert-butylphenyl | 1 | a | 54–56° | 65.29 | 65.4 | 7.53 | 7.5 | — | — |
| 13 | 4-phenoxyphenyl | 1 | a | 67–69° | 65.45 | 65.8 | 5.50 | 5.4 | 29.06 | 28.6 |
| 14 | 4-methoxyphenyl | 1 | a | 43.46° | 58.20 | 58.6 | 6.01 | 5.9 | 35.78 | 35.5 |

EXAMPLE A 0.1 g of the photo-initiators according to the invention is dissolved in 10.0 g of freshly distilled methyl acrylate. This solution is exposed, in a quartz glass tube 1.5 cm in diameter, in a thermostat-controlled water bath at 25°, to a high-pressure mercury vapour burner. The lamp is at a distance of 10 cm from the quartz tube. Prior to exposure, nitrogen is passed through the solution of the initiator for 1 minute and nitrogen also continues to be passed through during exposure. The polymerization which starts during exposure can be recognised by a rise in the temperature of the irradiated solution. The exposure time which elapses before the temperature rises in the solution is noted as the start time; the total exposure time is 20 seconds. Immediately after exposure, the exposed solution is cooled in order to prevent thermal polymerisation. The solution of the polymer formed, in the monomer, is rinsed into a round-bottomed flask using small amounts of ethyl acetate and the solvent and the unpolymerised monomeric constituent are then distilled off using a rotary evaporator. The polymeric residue is dried in a vacuum drying cabinet at 50°–60° and then weighed.

The values obtained with the photo-initiators according to the invention using the test arrangement described above are given in Table 3 which follows:

| Photo-initiator | Start time in seconds | Amount of polymer formed |
|---|---|---|
| Compound from Example 1 | 6 | 6.5% |
| Compound from Example 2 | 6 | 8% |
| Compound from Example 4 | 5 | 3.8% |
| Compound from Example 5 | 5 | 6.5% |
| Compound from Example 6 | 6 | 6% |
| Compound from Example 7 | 4 | 8% |
| Compound from Example 8 | 14 | 2.5% |
| Compound from Example 9 | 11 | 4.2% |
| Compound from Example 10 | 11 | 3% |
| Compound from Example 11 | 8 | 4.2% |

Without a photo-initiator, the amount of polymer is less than 0.1% and no rise in temperature takes place during exposure.

EXAMPLE B

A resin mixture consisting of 80 parts of Plex 6617 (acrylate resin from Messrs. Rohm, Darmstadt) and 20 parts of Plex 6618 (reactive diluent based on acrylate from Messrs. Rohm, Darmstadt) is mixed with 2 parts of the photo-initiators according to the invention and the mixture is spread in a thickness of 40 μm on glass plates using a film spreader. These films are exposed to the air for about 20 seconds and then irradiated with a medium-pressure Hg burner (HanoviaGerat, Model 45080). The samples are passed on a conveyor belt, under the UV lamp at a rate such that the effective exposure time is 0.16 second per pass.

Table 4 which follows gives the number of passes (P) which were necessary in order to obtain, with the photo-initiators according to the invention, films resistant to wiping. In addition, the hardness of the film was determined using a pendulum apparatus according to Konig.

Table 4

| Photo-initiator used | Passes necessary | Pendulum hardness according to Konig after 3P | Pendulum hardness according to Konig after 4P |
|---|---|---|---|
| methyl α-dimethoxy-benzoyl-acetate (Example 7) | 3–4 | 37 | 42 |
| ethyl α-diethoxy- | | | |

Table 4-continued

| Photo-initiator used | Passes necessary | Pendulum hardness according to Konig | |
|---|---|---|---|
| | | after 3P | after 4P |
| benzoyl-acetate (Example 1) | 3–4' | 33 | 38 |

Example C

A resin mixture consisting of 80 parts of Plex 6617 (acrylate resin from Messrs. Rohm, Darmstadt) and 20 parts of trismethylolpropane trisacrylate is mixed with 2 parts of the photo-initiators according to the invention and the mixture is spread in a thickness of 40 μm on glass plates using a film spreader. These films are exposed to the air for about 20 seconds and then irradiated with a medium-pressure Hg burner (Hanovia-Gerat, Model 45080). The samples are passed, on a conveyor belt, under the UV lamp at a rate such that the effective exposure time is 0.16 second per pass.

Table 5 which follows gives the number of passes (P) which were necessary in order to obtain, with the photo-initiators according to the invention, films resistant to wiping. In addition, the hardness of the film was determined using a pendulum apparatus according to Konig.

Table 5

| Photo-initiator | Passes necessary to achieve resistance to wiping | Pendulum hardness acccording to Konig, H, as a function of the number of passes P; H(P) |
|---|---|---|
| Compound from Example 1 | 14 | 49(3); 56(6); 113(14) |
| Compound from Example 2 | 8 | 120(8); 127(10) |
| Compound from Example 3 | 8 | 132(15); 137(17) |
| Compound from Example 4 | 9 | 120(15); 123(17) |
| Compound from Example 5 | 8 | 120(8); 132(10); 134(12) |
| Compound from Example 6 | 13 | 111(13); 112(5) |
| Compound from Example 7 | 10 | 66(3); 82(6); 100(10) |
| Compound from Example 8 | 10 | 127(10); 129(12); 133(14) |
| Compound from Example 9 | 3 | 92(3); 109(5); 116(7) |
| Compound from Example 10 | 8 | 112(8); 122(10); 126(12) |
| Compound from Example 11 | 9 | 120(9); 126(10); 134(12) |

What is claimed is:

1. In a method for the photo-polymerization of ethylemically unsaturated compounds, the improvement consisting substantially in the use as a photoinitiator of a compound of the formula I

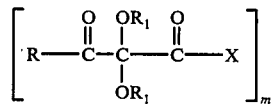

in which $m$ is 1 or 2,

R, when $m$ is 1, denotes a phenyl radical which can be substituted by one or more of the groups: alkyl with 1–4 C atoms, alkoxy or alkylthio with 1–4 C atoms, phenoxy, alkoxyalkyl with 2–4 C atoms, acylamino with 1–4 C atoms or halogen, or denotes a pyridyl radical and, when $m$ is 2, represents phenylene, $R_1$ represents alkyl with 1–6 C atoms, alkoxyalkyl with 3–6 C atoms, cycloalkyl with 5–7 C atoms, phenylalkyl with 7–9 C atoms, furfuryl, tetrahydrofurfuryl or phenyl, which can be substituted by one or more of the groups: alkyl with 1–4 C atoms, alkoxy or alkylthio with 1–4 C atoms, alkoxyalkyl with 2–4 C atoms, halogen or acylamino with 1–4 C atoms, X represents a group $-OR_2$ or $-N(R_3)(R_4)$, in which $R_2$ either represents one of the substituents mentioned for $R_1$ or is alkyl with 7–18 C atoms and $R_3$ and $R_4$ independently of one another represent hydrogen, alkyl with 1–4 C atoms, alkoxyalkyl with 3–6 C atoms or hydroxyalkyl with 2–4 C atoms.

2. A method according to claim 1 wherein $m$ is 1 or 2, R denotes a phenyl radical which can be substituted by $CH_3$, $OCH_3$, $OC_6H_5$, $SCH_3$ or Cl, or R represents a meta- or para-phenylene radical, $R_1$ is alkyl with 1–4 C atoms and X is a group $-OR_1$.

3. A photopolymerisable system consisting of at least one unsaturated photopolymerisable compound and 0.1 to 20% by weight of a compound of the formula I of claim 1

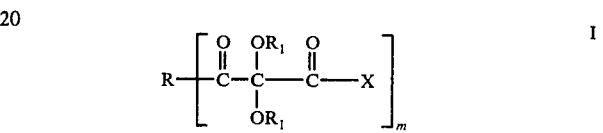

in which $m$ is 1 or 2, R, when $m$ is 1, denotes a phenyl radical which can be substituted by one or more of the groups: alkyl with 1–4 C atoms, alkoxy or alkylthio with 1–4 C atoms, phenoxy, alkoxyalkyl with 2–4 C atoms, acylamino with 1–4 C atoms or halogen, or denotes a pyridyl radical and, when $m$ is 2, represents phenylene, $R_1$ represents alkyl with 1–6 C atoms, alkoxyalkyl with 3–6 C atoms, cycloalkyl with 5–7 C atoms, phenylalkyl with 7–9 C atoms, furfuryl, tetrahydrofurfuryl or phenyl, which can be substituted by one or more of the groups: alkyl with 1–4 C atoms, alkoxy or alkylthio with 1–4 C atoms, alkoxyalkyl with 2–4 C atoms, halogen or acylamino with 1–4 C atoms, X represents a group $-OR_2$ or $-N(R_3)(R_4)$, in which $R_2$ either represents one of the substituents mentioned for $R_1$ or is alkyl with 7–18 C atoms and $R_3$ and $R_4$ independently of one another represent hydrogen, alkyl with 1–4 C atoms, alkoxyalkyl with 3–6 C atoms or hydroxyalkyl with 2–4 C atoms, as a photo-initiator.

4. A Photopolymerisable system according to claim 3 which contains a compound of the formula I in which $m$ is 1 or 2, R denotes a phenyl radical which can be substituted by $CH_3$, $OCH_3$, $OC_6H_5$, $SCH_3$ or Cl, or R represents a pyridyl radical or a meta- or para-phenylene radical, $R_1$ is alkyl with 1–4 C atoms and X is a group $-OR_1$, as a photo-initiator.

5. A Photopolymerisable system according to claim 3 which contains one or more esters of acrylic acid or methacrylic acid as the unsaturated compound.

6. A Photopolymerisable system according to claim 3 which contains an unsaturated polyester mixed with styrene as the unsaturated compound.

7. A Photopolymerisable system according to claim 3 which is a photopolymerisable printing paste.

8. A Photopolymerisable system according to claim 3 which is a photopolymerisable composition for the manufacture of printing plates.

9. A method according to claim 1 wherein X is a group $-N(R_3)(R_4)$, $R_3$ and $R_4$ independently of one another represent hydrogen, alkyl with 1–4 C atoms, alkoxyalkyl with 3–6 C atoms or hydroxyalkyl with 2–4 C atoms and $m$.

10. A method according to claim 1 of the formula

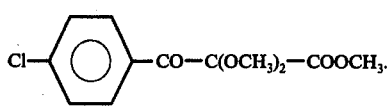
11. A method according to claim 1 of the formula
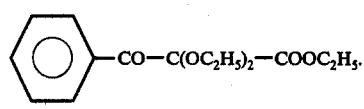
12. A method according to claim 1 of the formula
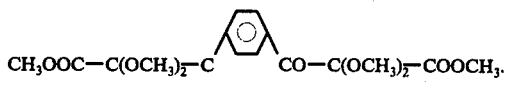
13. A method according to claim 1 of the formula
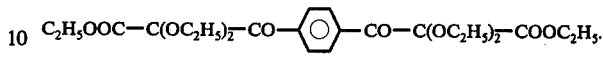
14. A photopolymerisable system of claim 3 wherein the photoinitiator of formula I is
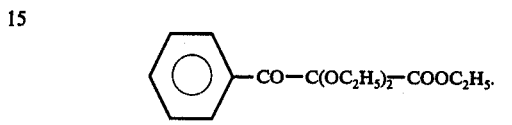
15. A photopolymerizable system of claim 3 wherein a compound of formula I is used in the concentration of 0.5 to 5% by weight.
* * * * *